United States Patent [19]

Junino et al.

[11] Patent Number: 5,279,620

[45] Date of Patent: * Jan. 18, 1994

[54] TINCTORIAL COMPOSITIONS FOR KERATIN FIBRES CONTAINING PRECURSORS OF OXIDATION COLORANTS AND INDOLE COUPLERS, AND DYEING PROCESSES USING THESE COMPOSITIONS

[75] Inventors: Alex Junino, Livry-Gargan; Gerard Lang, Saint-Gratien, both of France

[73] Assignee: L'Oreal, Paris, France

[*] Notice: The portion of the term of this patent subsequent to Jul. 23, 2008 has been disclaimed.

[21] Appl. No.: 871,116

[22] Filed: Apr. 20, 1992

Related U.S. Application Data

[63] Continuation of Ser. No. 404,569, Sep. 8, 1989, abandoned.

[30] Foreign Application Priority Data

Sep. 12, 1988 [LU] Luxembourg .................... 87337

[51] Int. Cl.$^5$ .............................. A61K 7/13
[52] U.S. Cl. .......................... 8/409; 8/407; 8/408; 8/410; 8/412; 8/414; 8/416; 8/421; 8/423
[58] Field of Search ............... 8/407, 408, 409, 410, 8/412, 414, 416, 421, 423

[56] References Cited

U.S. PATENT DOCUMENTS

| | | | |
|---|---|---|---|
| 4,013,404 | 3/1977 | Parent et al. ............... | 8/11 |
| 4,200,432 | 4/1980 | Kalopissis et al. ........... | 8/10.2 |
| 4,277,244 | 7/1981 | Bugaut et al. .............. | 8/410 |
| 4,425,132 | 1/1984 | Grollier et al. ............. | 8/405 |
| 4,545,978 | 10/1985 | Kalopissis et al. .......... | 8/405 |
| 4,932,977 | 6/1990 | Schultz ..................... | 8/423 |
| 5,021,067 | 6/1991 | Grollier .................... | 8/409 |
| 5,034,015 | 7/1991 | Junino et al. .............. | 8/423 |
| 5,053,053 | 10/1991 | De Labbey et al. ......... | 8/423 |
| 5,112,360 | 5/1992 | Garoche et al. ............ | 8/423 |
| 5,207,798 | 5/1993 | Cotteret et al. ............ | 8/408 |

FOREIGN PATENT DOCUMENTS

| | | |
|---|---|---|
| 0271186 | 6/1988 | European Pat. Off. . |
| 3031709 | 8/1980 | Fed. Rep. of Germany . |
| 1217479 | 5/1969 | United Kingdom . |
| 2207443 | 2/1989 | United Kingdom . |

Primary Examiner—Linda Skaling
Attorney, Agent, or Firm—Cushman, Darby & Cushman

[57] ABSTRACT

Tinctorial composition for keratin fibers, containing a para-type precursor of an oxidation colorant associated with a heterocyclic coupler of formula:

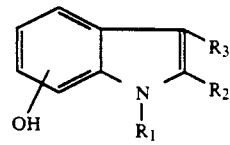

where $R_1=H$, or $C_1-C_4$alkyl; $R_2$ and $R_3$, which may be identical or different, denote H, $C_1-C_4$alkyl, carboxyl or alkoxycarbonyl; OH is in position 6 or 7;

and/or a salt of such a coupler.

This composition allows the hair to be dyed with a color having a good resistance to light, washing, bad weather and perspiration.

21 Claims, No Drawings

TINCTORIAL COMPOSITIONS FOR KERATIN FIBRES CONTAINING PRECURSORS OF OXIDATION COLORANTS AND INDOLE COUPLERS, AND DYEING PROCESSES USING THESE COMPOSITIONS

This is a continuation of application Ser. No. 07/404,569, filed Sep. 8, 1989, now abandoned.

The present invention relates to new tinctorial compositions for keratin fibres and in particular for human hair, containing precursors of oxidation colorants and indole couplers, and a dyeing process using such compositions.

It is known to dye keratin fibres, and in particular human hair, with tinctorial compositions containing precursors of oxidation colorants and in particular p-phenylenediamines or ortho- or para-aminophenols generally called "oxidation base".

It is also known that the hues obtained with these oxidation bases can be varied by using, in association with these bases, couplers which are also called color modifiers, and more particularly aromatic metadiamines, meta-aminophenols and meta-diphenols.

In the field of hair dyeing, precursors of oxidation colorants or of couplers are sought which allow a color having satisfactory resistance to light, to washing, to bad weather and to perspiration to be conferred to the hair in the oxidizing alkaline medium generally used in oxidation dyeing.

The applicants have just discovered, which is the subject of the invention, that the use of certain indole derivatives as couplers, with precursors of oxidation colorants of the para-type, allowed dyes having particularly remarkable resistance to light, to washing, to bad weather and to perspiration to be obtained after application on keratin fibres and in particular hair.

One subject of the invention therefore comprises oxidation tinctorial compositions, intended to be used for dyeing keratin fibres, containing at least one precursor of an oxidation colorant of the para-type with certain indole derivatives defined below.

Another subject of the invention comprises the process of coloration of keratin fibres, in particular of human hair, using such a composition.

Other subjects of the invention will appear on reading the description and the examples which follow.

The oxidation tinctorial composition according to the invention, which is intended to be used for dyeing keratin fibres and in particular hair, is essentially characterized in that it contains, in an acceptable solvent medium, at least one para- precursor of an oxidation colorant and at least one heterocyclic coupler corresponding to formula (I):

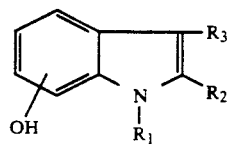

(I)

in which OH occupies positions 6 or 7 of the aromatic nucleus and $R_1$ designates a hydrogen atom or a $C_1$-$C_4$ alkyl radical; $R_2$ and $R_3$, which may be identical or different, designate a hydrogen atom, a $C_1$-$C_4$ lower alkyl radical, a carboxyl radical or a $C_1$-$C_4$ alkoxycarbonyl radical; as well as their salts.

Among the compounds of formula (I), the particularly preferred compounds are the compounds in which the alkyl radical designates methyl or ethyl and the alkoxycarbonyl radical designates methoxy- or ethoxycarbonyl.

Among these compounds, there may be mentioned 6-hydroxyindole, 6-hydroxy-3-methoxycarbonylindole, 6-hydroxy-1-methyl-3-methoxycarbonylindole, 6-hydroxy-1-methyl-2,3-dimethoxycarbonylindole, 6-hydroxy-1,2-dimethylindole, 6-hydroxy-2-methylindole, 6-hydroxy-2-carboxyindole, 6-hydroxy-2,3-dimethylindole, 6-hydroxy-3-carboxyindole, 6-hydroxy-3-ethoxycarbonylindole, 6-hydroxy-2-ethoxycarbonylindole, 6-hydroxy-3-methylindole, 6-hydroxy-1-methylindole, 7-hydroxyindole and 7-hydroxy-3-methylindole.

Among these compounds 6-hydroxy 1-methylindole and 7-hydroxy 3-methylindole are novel, their synthesis is described hereafter.

The colorant precursors of the para type are compounds which are not colorants in themselves, but which form a colorant by an oxidative condensation process, either with themselves, or in the presence of a coupler or modifier.

These compounds contain functional groups, in particular amino or hydroxyl groups, in the para-position with respect to each other.

These para-type colorant precursors are chosen in particular from the para-phenylenediamines, the para-aminophenols and the para-heterocyclic precursors such as 2,5-diaminopyridine, 2-hydroxy-5-aminopyridine and tetraaminopyrimidine.

As regards para-phenylenediamines, there may be more particularly mentioned the compounds which correspond to formula (II) below:

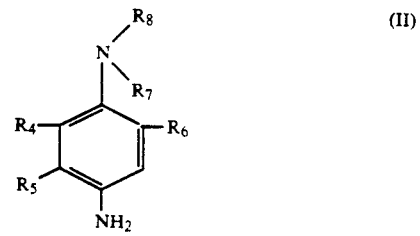

(II)

in which $R_4$, $R_5$ and $R_6$, which may be identical or different, represent a hydrogen or halogen atom, an alkyl radical having 1 to 4 carbon atoms or an alkoxy radical having 1 to 4 carbon atoms, $R_7$ and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical. These alkyl or alkoxy groups having from 1 to 4 carbon atoms, or again $R_7$ and $R_8$, form, together with the nitrogen atom to which they are bonded, a piperidino or morpholino heterocycle, with the reservation that $R_4$ or $R_6$ represent a hydrogen atom when $R_7$ and $R_8$ do not represent a hydrogen atom, as well as the salts of these compounds.

Among the compounds of formula (II), there may more particularly be mentioned p-phenylenediamine, p-toluylenediamine, methoxy-para-phenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di($\beta$-hydroxyethyl)para-phenylenediamine, 3-methyl-4-amino-N,N-di-($\beta$-hydroxyethyl)aniline, 3-chloro-4-amino-N,N-di-($\beta$-hydroxyethyl)aniline, 4-amino-N,N-(ethylcarbamylmethyl)aniline, 3-methyl-4-amino-N,N-(ethylcarbamylmethyl)aniline, 4-amino-N,N-(ethyl-$\beta$-piperidinoethyl)aniline, 3-methyl-4-amino-N,N-(ethyl-$\beta$-piperidinoethyl)aniline, 4-amino-N,N-(ethyl-$\beta$-morpholinoethyl)aniline, 3-methyl-4-amino-N,N-(ethyl-$\beta$-morpholinoethyl)aniline, 4-amino-N,N-(ethyl-$\beta$-acetylaminoethyl)aniline, 4-amino-N,N-($\beta$-methoxyethyl)aniline, 3-methyl-4-amino-N,N-(ethyl-$\beta$-acetylaminoethyl)aniline, 4-amino-N,N-(ethyl-$\beta$-mesylaminoethyl)aniline, 3-methyl-4-amino-N,N-(ethyl-$\beta$-mesylaminoethyl)aniline, 4-amino-N,N-(ethyl-$\beta$-sulphoethyl)aniline, 3-methyl-4-amino-N,N-(ethyl-$\beta$-sulphoethyl)aniline, N-[(4'-amino)phenyl]morpholine and N-[(4'-amino)phenyl]piperidine. These para-type precursors of oxidation colorants can be introduced into the tinctorial composition either in the form of the free base, or in the form of salts, such as in the form of hydrochloride, hydrobromide or sulphate.

Among the p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol and 3-methoxy-4-aminophenol.

The tinctorial compositions according to the invention can contain, in addition, ortho-type precursors of oxidation colorants, such as ortho-aminophenols such as 1-amino-2-hydroxybenzene, 6-methyl-1-hydroxy-2-aminobenzene or 4-methyl-1-amino-2-hydroxybenzene; orthophenylenediamines or ortho-diphenols.

The tinctorial compositions can also contain, in addition to the heterocyclic coupler corresponding to formula (I) above, other couplers which are known per se, such as meta-diphenols, meta-aminophenols, meta-phenylenediamines, meta-acylaminophenols, meta-ureidophenols, meta-carbalkoxyaminophenols, $\alpha$-naphthol or couplers having an active methylene group such as $\beta$-ketone compounds and pyrazolones.

In particular there may be mentioned as examples 2,4-dihydroxyphenoxyethanol, 2,4-dihydroxyanisole, meta-aminophenol, resorcinol monomethylether, 2-methyl-5-aminophenol, 2-methyl-N-($\beta$-hydroxyethyl)-5-aminophenol, 2-methyl-N-($\beta$-mesylaminoethyl)-5-aminophenol, 2,6-dimethyl-3-aminophenol, 6-hydroxybenzomorpholine, 2,4-diaminoanisole, 2,4-diaminophenoxyethanol, 6-aminobenzomorpholine, [N-($\beta$-hydroxyethyl)-2-amino-4-amino]phenoxyethanol, 2-amino-N-($\beta$-hydroxyethyl)-4-aminoanisole, (2,4-diamino)phenyl-$\beta$,$\gamma$-dihydroxypropylether and 2,4-diaminophenoxyethylamine and their salts.

There may be added to these compositions, as is well known in the state of the art, direct colorants such as azo colorants, anthraquinone colorants or nitrated derivatives of the benzene series, in particular with a view to shading or enriching with glints the colors afforded by the precursors of oxidation colorants.

All of the para-type precursors of oxidation colorants as well as the couplers used in the tinctorial compositions according to the invention preferably represent from 0.3 to 7% by weight with respect to the weight of the said composition. The concentration of compounds (I) can vary between 0.05 and 3.5% by weight of the total weight of the composition.

The acceptable solvent medium is generally aqueous, and its pH can vary between 8 and 11, and it is preferably between 9 and 11.

It is adjusted to the desired value with the aid of an alkalinizing agent such as ammonia, the alkali carbonates or the alkanolamines such as mono-, di- or triethanolamine.

The tinctorial compositions according to the invention also contain, in their preferred form of implementation, anionic, cationic, non-ionic or amphoteric surfactants or their mixtures. Among these surfactants there may be mentioned the alkylbenzenesulphonates, the alkylnaphthalenesulphonates, the sulphates, the ether sulphates and the sulphonates of fatty alcohols, quaternary ammonium salts such as trimethylcetylammonium bromide and cetylpyridinium bromide; optionally ethoxylated fatty acid ethanolamides; polyethoxylated acids, alcohols or amines, polyglycerolated alcohols or polyethoxylated or polyglycerolated alkylphenols, as well as polyethoxylated alkylsulphates.

These surfactants are present in the compositions according to the invention in proportions of between 0.5 and 55% by weight, and preferably between 2 and 50% by weight with respect to the total weight of the composition.

These compositions can also contain organic solvents to solubilize the compounds which would not be sufficiently soluble in water. Among these solvents, there may be mentioned as examples, the $C_1$–$C_4$ lower alkanols such as ethanol and isopropanol; glycerol; the glycols or glycol ethers such as 2-butoxyethanol, ethylene glycol, propylene glycol and the monoethyl ether and the monomethyl ether of diethyleneglycol, as well as the aromatic alcohols such as benzyl alcohol or phenoxyethanol, analogous products or their mixtures.

The solvents are preferably present in a proportion of between 1 and 40% by weight, and in particular between 5 and 30% by weight with respect to the total weight of the composition.

The thickening agents which can be added to the compositions according to the invention can be chosen in particular from sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. Inorganic thickening agents, such as bentonite, can also be used. These thickening agents are preferably present in proportions of between 0.1 to 5%, and in particular between 0.2 and 3% by weight with respect to the total weight of the composition.

The antioxidants which can be present in the compositions are chosen in particular from sodium sulphite, thioglycolic acid, sodium bisulphite, ascorbic acid and hydroquinone. These antioxidants are present in the composition in proportions of between 0.05 and 1.5% by weight with respect to the total weight of the composition.

These compositions can also contain other cosmetically acceptable additives, such as, for example, penetration agents, sequestering agents, buffers, fragrances and the like.

The compositions according to the invention can be presented in various forms, such as in the form of liquids, creams, gels, or in any other form which is appropriate for carrying out dyeing of keratin fibres and in particular human hair. These compositions can be packed in aerosol containers in the presence of a propellant.

The tinctorial compositions according to the invention which contain a para-type precursor of an oxidation colorant and a coupler of formula (I) are used in processes for dyeing keratin fibres, and in particular human hair, according to a process using development by means of an oxidizing agent.

According to this process, the tinctorial composition described above is mixed at the time of use with an oxidizing solution in sufficient quantity to develop a coloration, then the mixture obtained is applied on keratin fibres and in particular human hair.

The oxidizing solution contains oxidizing agents such as hydrogen peroxide, urea peroxide or persalts such as ammonium persulphate. A 20 volume solution of hydrogen peroxide is preferably used.

The mixture obtained is applied on the hair and left in place for 10 to 40 minutes, preferably 15 to 30 minutes, after which the hair is rinsed, washed with shampoo, rinsed again and dried.

The heterocyclic coupler of formula (I) defined above can also be used in a process of several stages, consisting in one of its stages in applying the para-precursor of an oxidation colorant by means of a composition defined above, and in another stage in applying the coupler of formula (I).

The oxidizing agent can be introduced into the composition applied in the second stage immediately before application, or again may be added onto the keratin fibres themselves in a third stage, the conditions of exposure and of drying or washing being identical.

The following examples are intended to illustrate the invention without, however, having a limiting character.

APPLICATION EXAMPLE 1

The following tinctorial mixture is prepared:

| | |
|---|---|
| 6-Hydroxyindole | 0.33 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| Ethomeen O 12 - Armoon Hess Chemical Company Ltd (oleylamine ethoxylated with 12 moles of ethylene oxide) | 4.5 g |
| Comperlan KD - Henkel Company (copra diethanolamide) | 9.0 g |
| Propylene glycol | 4.0 g |
| 2-Butoxyethanol | 8.0 g |
| 96% Ethanol | 6.0 g |
| Masquol DTPA - Protex Company (pentasodium diethylenetriaminepentacetate) | 2.0 g |
| Hydroquinone | 0.15 g |
| 35° Be sodium bisulphite solution | 1.3 g |
| 22° Be ammonia solution | 10.0 g |
| Water qs | 100.0 g |
| pH = 10.5 | |

100 g of 20 volume hydrogen peroxide is added at the time of use. The mixture, applied for 20 minutes at 34° C. on hair containing 90% naturally white hair, gives it, after shampooing and rinsing, a medium golden brown color.

APPLICATION EXAMPLE 2

The following tinctorial mixture is prepared:

| | |
|---|---|
| 6-Hydroxyindole | 0.33 g |
| p-Aminophenol | 0.27 g |
| Oleyl alcohol polyglycerolated with 2 moles of glycerol | 4.5 g |
| Oleyl alcohol polyglycerolated with 4 moles of glycerol | 4.5 g |
| Ethomeen O 12 - Armoon Hess Chemical Company Ltd. (oleylamine ethoxylated with 12 moles of ethylene oxide) | 4.5 g |
| Comperlan KD - Henkel Company (copra diethanolamine) | 9.0 g |
| Propylene glycol | 4.0 g |
| 2-Butoxyethanol | 8.0 g |
| 96% Ethanol | 6.0 g |
| Masquol DTPA - Protex Company (pentasodium diethylenetriaminepentacetate) | 2.0 g |
| Hydroquinone | 0.15 g |
| 35° Be sodium bisulphite solution | 1.3 g |
| 22° Be ammonia solution | 10.0 g |
| Water qs | 100.0 g |
| pH = 10.5 | |

100 g of 20 volume hydrogen peroxide is added at the time of use. The mixture, applied for 20 minutes at 34° C. on bleached hair, gives it, after shampooing and rinsing, a golden beige color.

APPLICATION EXAMPLE 3

The following tinctorial mixture is prepared:

| | |
|---|---|
| 6-Hydroxy-1-methylindole | 0.73 g |
| Bis-(β-hydroxyethyl)-4-aminoaniline dihydrochloride | 1.34 g |
| Cellosize WP 03 - Union Carbide Company (hydroxyethylcellulose) | 2.0 g |
| Ammonium laurylsulphate | 5.0 g |
| 2-Butoxyethanol | 15.0 g |
| 96% Alcohol | 5.0 g |
| Masquol DTPA - Protex Company (pentasodium diethylenetriaminepentacetate) | 2.0 g |
| Water qs | 100.0 g |
| pH = 10.5 | |

100 g of 20 volume hydrogen peroxide is added at the time of use. The mixture, applied for 20 minutes at 34° C. on hair containing 90% naturally white hair, gives it, after shampooing and rinsing, a dark purple-grey color.

APPLICATION EXAMPLE 4

The following tinctorial mixture is prepared:

| | |
|---|---|
| 6-Hydroxy-1-methylindole | 0.29 g |
| Para-phenylenediamine | 0.22 g |
| Octyldodecanol sold under the name of Eutanol G by the Henkel Company | 8.0 g |
| Oleic acid | 20.0 g |
| Monoethanolamine laurylethersulphate sold under the name of Sipon LM 35 by the Henkel Company | 3.0 g |
| Ethyl alcohol | 10.0 g |
| Benzyl alcohol | 10.0 g |
| Cetylstearyl alcohol ethoxylated with 33 moles of ethylene oxide, sold under the name of Simulsol GS by the Seppic Company | 2.4 g |
| Ethylenediaminetetraacetic acid | 0.2 g |
| Cationic polymer consisting of recurrent units: | 2.2 g |

-continued

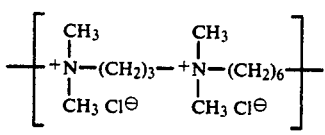

| | |
|---|---|
| Monoethanolamine | 7.5 g |
| Linoleic acid diethanolamide sold under the name of Comperlan F by the Henkel Company | 8.0 g |
| 20% Ammonia solution | 10.2 g |
| 35% Aqueous solution of sodium metabisulfite | 1.3 g |
| Hydroquinone | 0.15 g |
| 1-Phenyl-3-methyl-5-pyrazolone | 0.2 g |
| Demineralized water qs | 100.0 g |

The composition is mixed weight for weight with 20 volume hydrogen peroxide, the pH of which is equal to 3, at the time of use.

The mixture thus obtained is applied for 30 minutes on grey hair containing 90% white hair, then the hair is rinsed, washed, rinsed again and dried.

The color obtained is a coppery beige blonde.

APPLICATION EXAMPLE 5

The following tinctorial mixture is prepared:

| | |
|---|---|
| 6-Hydroxy-2-ethoxycarbonylindole | 0.41 g |
| Para-phenylenediamine | 0.22 g |
| Octyldodecanol sold under the name of Eutanol G by the Henkel Company | 8.0 g |
| Oleic acid | 20.0 g |
| Monoethanolamine laurylethersulphate sold under the name of Sipon LM 35 by the Henkel Company | 3.0 g |
| Ethyl alcohol | 10.0 g |
| Benzyl alcohol | 10.0 g |
| Cetylstearyl alcohol ethoxylated with 33 moles of ethylene oxide, sold under the name of Simulsol GS by Seppic Company | 2.4 g |
| Ethylenediaminetetraacetic acid | 0.2 g |
| Cationic polymer consisting of recurrent units: | 2.2 g |

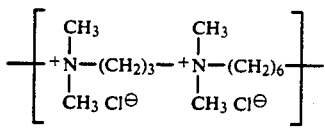

| | |
|---|---|
| Monoethanolamine | 7.5 g |
| Linoleic acid diethanolamide sold under the name of Comperlan F by the Henkel Company | 8.0 g |
| 20% Ammonia solution | 10.2 g |
| 35% Aqueous solution of sodium metabisulphite | 1.3 g |
| Hydroquinone | 0.15 g |
| 1-Phenyl-3-methyl-5-pyrazolone | 0.2 g |
| Demineralized water qs | 100.0 g |

The composition is mixed weight for weight with 20 volume hydrogen peroxide, the pH of which is equal to 3, at the time of use.

The mixture thus obtained is applied for 30 minutes on grey hair containing 90% white hair, then the hair is rinsed, washed, rinsed again and dried.

The color obtained is an ash beige-blonde.

APPLICATION EXAMPLE 6

The following tinctorial mixture is prepared:

| | |
|---|---|
| 6-Hydroxy-2-carboxyindole | 0.35 g |
| Para-phenylenediamine | 0.22 g |
| Octyldodecanol sold under the name of Eutanol G by the Henkel Company | 8.0 g |
| Oleic acid | 20.0 g |
| Monoethanolamine laurylethersulphate sold under the name of Sipon LM 35 by the Henkel Company | 3.0 g |
| Ethyl alcohol | 10.0 g |
| Benzyl alcohol | 10.0 g |
| Cetylstearyl alcohol ethoxylated with 33 moles of ethylene oxide sold under the name of Simulsol GS by the Seppic Company | 2.4 g |
| Ethylenediaminetetraacetic acid | 0.2 g |
| Cationic polymer consisting of recurrent units: | 2.2 g |

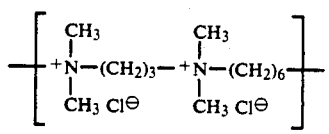

| | |
|---|---|
| Monoethanolamine | 7.5 g |
| Linoleic acid diethanolamide sold under the name of Comperlan F by the Henkel Company | 8.0 g |
| 20% Ammonia solution | 10.2 g |
| 35% Aqueous solution of sodium metabisulphite | 1.3 g |
| Hydroquinone | 0.15 g |
| 1-Phenyl-3-methyl-5-pyrazolone | 0.2 g |
| Demineralized water qs | 100.0 g |

The composition is mixed weight for weight with 20 volume hydrogen peroxide, the pH of which is equal to 3, at the time of use.

The mixture thus obtained is applied for 30 minutes on grey hair containing 90% white hair, then the hair is rinsed, washed, rinsed again and dried.

The color is dark coppery beige blonde.

APPLICATION EXAMPLE 7

Example 6 is reproduced by using 0.29 g of 7-hydroxy 3-methyl indole instead of the 0.35 g of 6-hydroxy 2-carboxyindole.

The dyeing conditions are the same as in example 6.

The color of the hair is irised light blond mahogany.

APPLICATION EXAMPLE 8

Example 6 is reproduced by using 0.32 g of 6-hydroxy 2,3-dimethyl indole instead of the 0.35 g of 6-hydroxy carboxyindole.

The dyeing conditions are the same as in example 6.

The hair is dyed in an irised light blond.

APPLICATION EXAMPLE 9

The following tinctorial mixture is prepared:

| | |
|---|---|
| 7-Hydroxyindole | 0.27 g |
| p-Phenylenediamine | 0.22 g |
| Octyldodecanol sold under the name of Eutanol G by the Henkel Company | 8.0 g |
| Oleic acid | 20.0 g |
| Monoethanolamine laurylethersulphate sold under the name of Sipon LM 35 by the Henkel Company | 3.0 g |
| Ethyl alcohol | 10.0 g |

| | |
|---|---|
| Benzyl alcohol | 10.0 g |
| Cetylstearyl alcohol ethoxylated with 33 moles of ethylene oxide sold under the name of Simulsol GS by the Seppic Company | 2.4 g |
| Ethylenediaminetetraacetic acid | 0.2 g |
| Cationic polymer consisting of recurrent units: | 2.2 g |

$$\left[ -{}^{+}\underset{\underset{CH_3 \; Cl^{\ominus}}{|}}{\overset{\overset{CH_3}{|}}{N}}-(CH_2)_3-{}^{+}\underset{\underset{CH_3 \; Cl^{\ominus}}{|}}{\overset{\overset{CH_3}{|}}{N}}-(CH_2)_6- \right]$$

| | |
|---|---|
| Monoethanolamine | 7.5 g |
| Linoleic acid diethanolamide sold under the name of Comperlan F by the Henkel Company | 8.0 g |
| 20% Ammonia solution | 10.2 g |
| 35% Aqueous solution of sodium metabisulphite | 1.3 g |
| Hydroquinone | 0.15 g |
| 1-Phenyl-3-methyl-5-pyrazolone | 0.2 g |
| Demineralized water qs | 100.0 g |

The composition is mixed weight for weight with 20 volume hydrogen peroxide, the pH of which is equal to 3, at the time of use.

The mixture thus obtained is applied for 30 minutes on grey hair containing 90% white hair, then the hair is rinsed, washed, rinsed again and dried.

The color is a dark ash pearly blonde.

APPLICATION EXAMPLE 10

The following tinctorial mixture is prepared:

| | |
|---|---|
| 7-Hydroxyindole | 0.53 g |
| p-Aminophenol | 0.44 g |
| Octyldodecanol sold under the name of Eutanol G by the Henkel Company | 8.0 g |
| Oleic acid | 20.0 g |
| Monoethanolamine laurylethersulphate sold under the name of Sipon LM 35 by the Henkel Company | 3.0 g |
| Ethyl alcohol | 10.0 g |
| Benzyl alcohol | 10.0 g |
| Cetylstearyl alcohol ethoxylated with 33 moles of ethylene oxide sold under the name of Simulsol GS by the Seppic Company | 2.4 g |
| Ethylenediaminetetraacetic acid | 0.2 g |
| Cationic polymer consisting of recurrent units: | 2.2 g |

$$\left[ -{}^{+}\underset{\underset{CH_3 \; Cl^{\ominus}}{|}}{\overset{\overset{CH_3}{|}}{N}}-(CH_2)_3-{}^{+}\underset{\underset{CH_3 \; Cl^{\ominus}}{|}}{\overset{\overset{CH_3}{|}}{N}}-(CH_2)_6- \right]$$

| | |
|---|---|
| Monoethanolamine | 7.5 g |
| Linoleic acid diethanolamide sold under the name of Comperlan F by the Henkel Company | 8.0 g |
| 20% Ammonia solution | 10.2 g |
| 35% Aqueous solution of sodium metabisulphite | 1.3 g |
| Hydroquinone | 0.15 g |
| 1-Phenyl-3-methyl-5-pyrazolone | 0.2 g |
| Demineralized water qs | 100.0 g |

The composition is mixed weight for weight with 20 volume hydrogen peroxide, the pH of which is equal to 3, at the time of use.

The mixture thus obtained is applied for 30 minutes on grey hair containing 90% white hair, then the hair is rinsed, washed, rinsed again and dried.

The color is a coppery pearly blonde.

APPLICATION EXAMPLE 11

Locks of hair containing 90% white hair are dyed with a composition (A9) having the following composition:

| | |
|---|---|
| -Hydroxyindole | 2.0 g |
| Ethanol | 10.0 g |
| Sodium laurylethersulphate | 1.0 g |
| Water qs | 100.0 g |

The exposure time is 10 minutes. After rinsing and drying a grey lock of hair with golden highlights is thus obtained.

By applying thereafter during 3 minutes a mixture in equal amounts of a 0,5% solution of N,N-bis-β-hydroxyethyl paraphenylenediamine in water and a hydrogen peroxide solution in water at 6% (pH 7) a lock colored in a dark blond with purple shades is obtained after rinsing and drying.

APPLICATION EXAMPLE 12

A 2.5% aqueous-alcoholic solution of 6-hydroxyindole is prepared at pH 9 (NAOH) and applied to hair at a rate of 2.5 g per g of grey hair. After 10 minutes exposure time, rinsing and drying, slightly ash blonde grey hair is obtained.

If a mixture of equal parts of a 0.5% solution of N-methoxyethyl-para-phenylenediamine at pH 10 and of 6% hydrogen peroxide is then applied for 3 minutes, hair of a light purple-chestnut color is obtained after rinsing and drying.

PREPARATION EXAMPLE 1

Preparation of 6-hydroxy-1-methylindole

1st stage: Preparation of 6-benzyloxy-1-methylindole 300 ml of toluene, 50 ml of methylsulphate and 7.36 g of tetrabutylammonium hydrogen sulphate are added to 125 g of sodium hydroxide pellets in 125 ml of water, then, with stirring, 0.33 mole (73.6 g) of 6-benzyloxyindole. Stirring is maintained for 15 minutes after the end of the evolution of heat. The reaction medium is diluted with 2 volumes of water. After separation of the organic phase, the aqueous phase is extracted with toluene. After washing the organic phases with water and drying them, the desired product is obtained by evaporation. It melts at 79° C.

Analysis of the product obtained after recrystallization from methanol gives the following results:

| Analysis for | Calculated for $C_{16}H_{15}NO$ | Found |
|---|---|---|
| C | 81.01 | 80.92 |
| H | 6.33 | 6.36 |
| N | 5.91 | 5.80 |
| O | 6.75 | 6.99 |

2nd stage: Preparation of 6-hydroxy-1-methylindole

The mixture consisting of 0.24 mole (57 g) of 6-benzyloxy-1-methylindole, 5.7 g of 10% palladium-on-charcoal, 114 ml of cyclohexene and 170 ml of 96% ethanol is heated for 30 minutes under reflux. The mixture is filtered hot to remove the catalyst. After evaporation of the filtrate under vacuum, an oil is obtained which, dissolved in isopropyl ether, gives the desired product after evaporation to dryness. It melts at 74° C.

Analysis of the product obtained gives the following results:

| Analysis for | Calculated for $C_9H_9NO$ | Found |
| --- | --- | --- |
| C | 73.47 | 73.57 |
| H | 6.12 | 6.12 |
| N | 9.52 | 9.39 |
| O | 10.88 | 11.07 |

PREPARATION EXAMPLE 2

Preparation of 7-hydroxy-3-methylindole

1st stage:

Preparation of 1-[(3'-benzylozy-5'-chloro-2'-nitro)phenyl]-2-cyanopropane

The reaction mixture consisting of 0.5 mole (151.2 g) of 3-benzyloxy-5-chloro-2-nitrophenylacetonitrile, 152.6 g of methyl iodide and 207 g of potassium carbonate in 500 ml of acetone is taken to reflux for 8 hours. The reaction medium is diluted with 4 kg of iced water to which has been added 500 ml of acetic acid. The desired product precipitates. After recrystallization from acetic acid it melts at 180° C.

Analysis of the product obtained gives the following results:

| Analysis from | Calculated for $C_{16}H_{13}N_2O_3Cl$ | Found |
| --- | --- | --- |
| C | 60.67 | 60.72 |
| H | 4.14 | 4.12 |
| N | 8.84 | 8.64 |
| O | 15.15 | 15.01 |
| Cl | 11.19 | 11.34 |

2nd stage: Preparation of 7-hydroxy-3-methylindole

The reaction mixture consisting of 20 g of 1-[(3'-benzyloxy-5'-chloro-2'-nitro)phenyl]-2-cyanopropane and 10 g of 10% palladium-on-charcoal in 100 ml of ethanol to which has been added 40 ml of cyclohexene is heated under reflux for 4 hours. At the end of the reaction the catalyst is separated from the reaction medium by filtration. After addition of carbon black to the filtrate, filtration and then evaporation, the desired product, which crystallizes from an isopropyl-ether-chloroform mixture, is obtained. It melts at 190° C.

Analysis of the product obtained gives the following results:

| Analysis for | Calculated for $C_9H_9NO$ | Found |
| --- | --- | --- |
| C | 73.45 | 73.53 |
| H | 6.16 | 6.23 |
| N | 9.52 | 9.45 |
| O | 10.87 | 10.76 |

We claim:

1. Tinctorial composition for keratin fibers containing, in a medium having a pH between 8 and 11 which is appropriate for dyeing said fibers, at least one para-type precursor of an oxidation colorant selected from the group consisting of para-phenylenediamines, para-aminophenols and para-heterocyclic precursors, in association with at least one heterocyclic coupler corresponding to the formula:

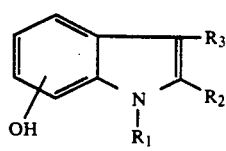

(I)

in which OH occupies positions 6 or 7 of the aromatic nucleus and $R_1$ represents a hydrogen atom or a $C_1$-$C_4$ alkyl radical; $R_2$ or $R_3$, which may be identical or different, designate a hydrogen atom, $C_1$-$C_4$ lower alkyl radical, a carboxyl radical or a $C_1$-$C_4$ alkoxy carbonyl radical; as well as their salts, the amount of said para-type precursor in said composition being sufficient to dye said keratin fibers and the amount of said heterocyclic coupler ranging from 0.05 to 3.5 percent by weight based on the total weight of said composition.

2. Composition according to claim 1, wherein the compounds of formula (I) are chosen from 6-hydroxyindole, 6-hydroxy-3-methoxycarbonylindole, 6-hydroxy-1-methyl-3-methoxycarbonylindole, 6-hydroxy-1-methyl-2,3-dimethoxycarbonylindole, 6-hydroxy-1,2-dimethylindole, 6-hydroxy-2-methylindole, 6-hydroxy-2-carboxyindole, 6-hydroxy-2,3-dimethylindole, 6-hydroxy-3-carboxyindole, 6-hydroxy-3-ethoxycarbonylindole, 6-hydroxy-2-ethoxycarbonylindole, 6-hydroxy-3-methylindole, 6-hydroxy-1-methylindole, 7-hydroxyindole and 7-hydroxy-3-methylindole.

3. Composition according to claim 1, wherein the para-phenylenediamines correspond to formula (II):

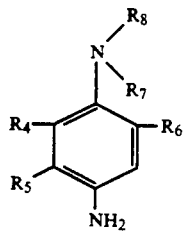

(II)

in which $R_4$, $R_5$ and $R_6$, which may be identical or different, represent a hydrogen or halogen atom, an alkyl radical having 1 to 4 carbon atoms or an alkoxy radical having 1 to 4 carbon atoms, $R_7$ and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, these alkyl or alkoxy groups having from 1 to 4 carbon atoms, or again R₇ and R₈, form, together with the nitrogen atom to which they are bonded, a piperidino or morpholino heterocycle, with the reservation that R₄ or R₆ represent a hydrogen atom when R₇ and R₈ do not represent a hydrogen atom, as well as the salts of these compounds.

4. Composition according to claim 3 wherein the compound having formula (II) is p-phenylenediamine, p-tolylenediamine, methoxy-para-phenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di(β-hydroxyethyl)para-phenylenediamine, 3-methyl-4-amino-N,N-di-(β-hydroxyethyl) aniline, 3-chloro-4-amino-N,N-di-(β-hydroxyethyl)aniline, 4-amino-N,N-(ethylcarbamylmethyl)aniline, 3-methyl-4-amino-N,N-(ethylcarbamylmethyl)aniline, 4-amino-N,N-(ethyl-β-piperidinoethyl)aniline, 3-methyl-4-amino-N,N-(ethyl-β-piperidinoethyl)aniline, 4-amino-N,N-(ethyl-β-morpholinoethyl) aniline, 3-methyl-4-amino-N,N-(ethyl-β-morpholinoethyl)aniline, 4-amino-N,N-(ethyl-β-acetylaminoethyl)aniline, 4-amino-N-(β-methoxyethyl)aniline, 3-methyl-4-amino-N,N-(ethyl-β-acetylaminoethyl)aniline, 4-amino-N,N-(ethyl-β-mesylaminoethyl) aniline, 3-methyl-4-amino-N,N-(ethyl-β-mesylaminoethyl)aniline, 4-amino-N,N-(ethyl-β-sulphoethyl)aniline, 3-methyl-4-amino-N,N-(ethyl-β-sulphoethyl)aniline, N-[(4'-amino)-phenyl]morpholine or N[(4'-amino)phenyl]piperidine or a salt thereof.

5. Composition according to claim 1 wherein the p-aminophenols are
p-aminophenol, 2-methyl-4-aminophenol, 3-methyl-4-aminophenol, 2-chloro-4-aminophenol, 3-chloro-4-amino-phenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol or 3-methoxy-4-aminophenol.

6. Composition according to claim 1 containing, in addition, an effective amount of ortho-type precursors of oxidation colorants selected from the group consisting of ortho-aminophenols, ortho-phenylenediamines and ortho-diphenols.

7. Composition according to claim 1, further containing in addition to the heterocyclic couplers of formula (I), at least one coupler selected from the group consisting of meta-diphenols, meta-aminophenols, meta-phenylenediamines, meta-acylaminophenols, meta-ureidophenols, meta-carbalkoxyaminophenols, α-naphthol, β-ketone compounds and pyrazolones.

8. Composition according to claim 7, wherein the couplers which are different from the heterocyclic couplers of formula (I) are chosen from 2,4-dihydroxyphenoxyethanol, 2,4-dihydroxyanisol, meta-aminophenol, resorcinol monoethylether, 2-methyl-5-aminophenol, 2-methyl-N-(β-hydroxyethyl)-5-aminophenol, 2-methyl-N-(β-mesylaminoethyl)-5-aminophenol, 2,6-dimethyl-3-aminophenol, 6-hydroxybenzomorpholine, 2,4-diaminoanisole, 2,4-diaminophenoxyethanol, 6-aminobenzomorpholine, [N-(β-hydroxyethyl)-2-amino-4-amino]-phenoxyethanol, 2-amino-N-(β-hydroxyethyl)-4-aminoanisole, (2,4-diamino)phenyl-β,γ-dihydroxypropylether and 2,4-diaminophenoxyethylamine and their salts.

9. Composition according to claim 1, further containing direct colorants in an effective amount.

10. Composition according to claim 1, wherein the para-type oxidation colorants and the couplers are present in proportions of between 0.3 and 7% by weight with respect to the total weight of the composition.

11. Composition according to claim 1, further containing anionic, cationic, nonionic or amphoteric surfactants or their mixtures in an amount of between 0.5–55% by weight with respect to the total weight of said composition.

12. Composition according to claim 1, further containing an organic solvent in proportions of between 1 and 40% by weight with respect to the total weight of the composition.

13. Composition according to claim 1, further containing an effective amount of at least one of a thickening agent, an antioxidant, a penetration agent, a sequestering agent, a buffer or a fragrance.

14. The composition according to claim 1, in the form of a liquid, a cream or a gel optionally packed in an aerosol container in the presence of a propellant.

15. A process for the preparation of a tinctorial composition, for keratin fibers, to be applied immediately on human hair, wherein said tinctorial composition contains in a medium having a pH between 8 and 11 which is appropriate for dyeing said fibers, at least one para-type precursor of an oxidation colorant selected from the group consisting of para-phenylenediamines, para-aminophenols and para-heterocyclic precursors, in association with at least one heterocyclic coupler corresponding to the formula:

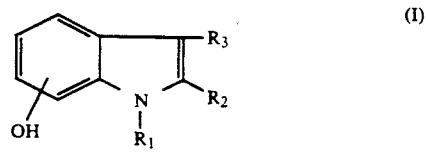

in which OH occupies positions 6 or 7 of the aromatic nucleus and R₁ represents a hydrogen atom or a C₁–C₄ alkyl radical; R₂ or R₃, which may be identical or different, designate a hydrogen atom, C₁–C₄ lower alkyl radical, a carboxyl radical or a C₁–C₄ alkoxy carbonyl radical; as well as their salts, the amount of said para-type precursor in said composition being sufficient to dye said keratin fibers and the amount of said heterocyclic coupler ranging from 0.05 to 3.5 percent by weight based on the total weight of said composition, said process comprising the step of mixing at the time of use said composition with an oxidizing solution in sufficient quantity to form a colorant.

16. Process for dyeing keratin fibers comprising the steps of:
applying to said fibers a composition containing, in a medium having a pH between 8 and 11, at least one para-type precursor of an oxidation colorant selected from the group consisting of para-phenylenediamines, para-aminophenols and para-heterocyclic precursors, in association with at least one heterocyclic coupler corresponding to the formula:

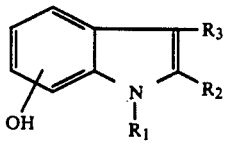

in which OH occupies positions 6 or 7 of the aromatic nucleus and $R_1$ represents a hydrogen atom or a $C_1$–$C_4$ alkyl radical; $R_2$ or $R_3$, which may be identical or different, designate a hydrogen atom, $C_1$–$C_4$ lower alkyl radical, a carboxyl radical or a $C_1$–$C_4$ alkoxy carbonyl radical; as well as their salts, the amount of said para-type precursor in said composition being sufficient to dye said keratin fibers and the amount of said heterocyclic coupler ranging from 0.5 to 3.5 percent by weight based on the total weight of said composition, said composition being applied in the presence of an effective amount of an oxidizing agent, wherein the composition is left in contact with said fibers for 10 to 40 minutes,
rinsing said fibers;
washing said fibers at least one time;
rinsing said fibers; and
drying said fibers such that dyed keratin fibers are obtained.

17. Process for dyeing keratin fibers comprising applying in a first step a composition comprising a para-precursor of an oxidation colorant, said para-precursor being selected from the group consisting of para-phenylenediamines, para-aminophenols and para-heterocylic precursors, to said keratin fibers, the amount of said para-precursor in said composition being sufficient to dye said keratin fibers, and, in a second step, applying a composition comprising at least one heterocyclic coupler having the formula:

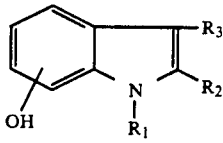

wherein OH occupies positions 6 or 7 of the aromatic nucleus and $R_1$ represents hydrogen or $C_1$–$C_4$ alkyl; $R_2$ and $R_3$, each independently represent hydrogen, $C_1$–$C_4$ lower alkyl, carboxyl or $C_1$–$C_4$ alkoxycarbonyl, or a salt thereof, to said keratin fibers, the amount of said coupler ranging from 0.05 to 3.5 percent by weight based on the total weight of said composition, and introducing an effective amount of an oxidizing agent selected from the group consisting of hydrogen peroxide, urea peroxide, and persalts, just before use, in combination with said heterocyclic coupler or applying said oxidizing agent to said keratinic fibers in a third step, the pH of said colorant, coupler, and oxidizing agent being between 8 and 11.

18. A tinctorial composition for dyeing keratin fibers comprising, in a medium having a pH between 8 and 11 suitable for dyeing said fibers, at least one para-type precursor of an oxidation colorant selected from the group consisting of a para-phenylenediamine, a para-aminophenol and a para-heterocyclic precursor, present in an amount ranging from 0.3 to 7 percent by weight based on the total weight of said composition, in association with at least one heterocyclic coupler having the formula

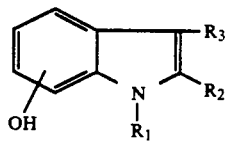

in which OH occupies positions 6 or 7 of the aromatic nucleus and $R_1$ represents hydrogen or a $C_1$–$C_4$ alkyl; $R_2$ or $R_3$, each independently, represent hydrogen, $C_1$–$C_4$ lower alkyl, carboxyl or $C_1$–$C_4$ alkoxycarbonyl, and the salts thereof, said heterocyclic coupler being present in an amount ranging from 0.05 to 3.5 percent by weight based on the total weight of said composition.

19. A tinctorial composition for dyeing keratin fibers comprising, in a medium having a pH between 8 and 11 suitable for dyeing said fibers at least one para-type precursor of an oxidation colorant selected from the group consisting of a para-phenylenediamine, a para-aminophenol and a para-heterocyclic precursor, present in an amount ranging from 0.3 to 7 percent by weight based on the total weight of said composition, in association with at least one heterocyclic coupler selected from the group consisting of 6-hydroxyindole, 6-hydroxy-3-methoxycarbonylindole, 6-hydroxy-1-methyl-3-methoxycarbonylindole, 6-hydroxy-1-methyl-2,3-dimethoxycarbonylindole, 6-hydroxy-1,2-dimethylindole, 6-hydroxy-2-methylindole, 6-hydroxy-2-carboxyindole, 6-hydroxy-2,3-dimethylindole, 6-hydroxy-3-carboxyindole, 6-hydroxy-3-ethoxycarbonylindole, 6-hydroxy-2-ethoxycarbonylindole, 6-hydroxy-3-methylindole, 6-hydroxy-1-methylindole, 7-hydroxyindole and 7-hydroxy-3-methylindole, said heterocyclic coupler being present in an amount ranging from 0.05 to 3.5 percent by weight based on the total weight of said composition.

20. The composition of claim 19 wherein said heterocyclic coupler is 6-hydroxyindole.

21. The composition of claim 19 wherein said heterocyclic coupler is 7-hydroxyindole.

* * * * *

UNITED STATES PATENT AND TRADEMARK OFFICE
CERTIFICATE OF CORRECTION

PATENT NO. : 5,279,620
DATED : January 18, 1994
INVENTOR(S) : Junino, et al

It is certified that error appears in the above-indentified patent and that said Letters Patent is hereby corrected as shown below:

On the Title Page, Item [75]: after "Saint-Gratien," add to the inventors, --Jean Jacques Vandenbossche, Aulnay-sous-Bois,--; and change "both" to --all--.

Signed and Sealed this

Thirty-first Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,279,620
DATED        : January 18, 1994
INVENTOR(S)  : Junino et al It is certified that error appears in the above-indentified patent and that said Letters Patent is hereby corrected as shown below:

On the title page, Item [75]: Inventors, please add --Jean Jacques Vandenbossche, Aulnay-sous-Bois, and change "both" to --all--

Signed and Sealed this

Twenty-first Day of June, 1994

Attest:

BRUCE LEHMAN

*Attesting Officer*    *Commissioner of Patents and Trademarks*